(12) United States Patent
Fukuzawa et al.

(10) Patent No.: US 10,123,913 B2
(45) Date of Patent: Nov. 13, 2018

(54) PULL-ON DIAPER

(71) Applicant: UNICHARM CORPORATION, Shikokuchuo-shi, Ehime (JP)

(72) Inventors: Masumi Fukuzawa, Kanonji (JP); Shunsuke Masaki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 371 days.

(21) Appl. No.: 14/765,837

(22) PCT Filed: Jan. 21, 2014

(86) PCT No.: PCT/JP2014/051043
§ 371 (c)(1),
(2) Date: Aug. 5, 2015

(87) PCT Pub. No.: WO2014/122979
PCT Pub. Date: Aug. 14, 2014

(65) Prior Publication Data
US 2015/0374559 A1    Dec. 31, 2015

(30) Foreign Application Priority Data
Feb. 6, 2013   (JP) .................................. 2013-021828

(51) Int. Cl.
*A61F 13/49*    (2006.01)
*A61F 13/496*   (2006.01)

(52) U.S. Cl.
CPC .. *A61F 13/49011* (2013.01); *A61F 13/49017* (2013.01); *A61F 13/4963* (2013.01); *A61F 2013/49088* (2013.01)

(58) Field of Classification Search
CPC ..................... A61F 13/49011; A61F 13/49017
See application file for complete search history.

(56) References Cited

U.S. PATENT DOCUMENTS 9,387,138 B2 *   7/2016   Roe ................... A61F 13/49003
2010/0249743 A1  9/2010   Takino
(Continued)

FOREIGN PATENT DOCUMENTS

GB   2474587 A  *  4/2011  ........... A61F 13/496
JP   10-52456 A    2/1998
(Continued)

OTHER PUBLICATIONS

Decision to Grant a Patent in JP Application No. 2013-021828, dated Mar. 7, 2017.
(Continued)

*Primary Examiner* — Tatyana Zalukaeva
*Assistant Examiner* — Gabriella Burnette
(74) *Attorney, Agent, or Firm* — Hauptman Ham, LLP

(57) ABSTRACT

In a pull-on diaper, a first distance dimension between outer end portions of front and rear waist panels is in a range of 300 mm to 400 mm as measured on the diaper flatly developed after coupling of the front and rear waist panels in seam regions has been released. A second distance dimension between the waist elastic closest to an inner end portion of the front waist panel among waist elastics extending in the front waist panel across the respective seam regions in the front waist panel and the waist elastic closest to an inner end portion of the rear waist panel among waist elastics extending in the rear waist panel across the respective seam regions is at least 55% of the first distance dimension between outer end portions of the front and rear waist panels.

6 Claims, 5 Drawing Sheets

(56) References Cited

U.S. PATENT DOCUMENTS

2012/0046632 A1  2/2012 Malowaniec
2015/0366724 A1* 12/2015 Fukuzawa ............ A61F 13/496
                                                    604/385.01

FOREIGN PATENT DOCUMENTS

| JP | 2009-61052 A  | 3/2009  |
| JP | 2009-160129 A | 7/2009  |
| JP | 2012-523868 A | 10/2012 |

OTHER PUBLICATIONS

International Search Report dated Apr. 22, 2014 in International Application No. PCT/JP2014/051043.

\* cited by examiner

PULL-ON DIAPER

RELATED APPLICATIONS

The present application is a National Phase of International Application Number PCT/JP2014/051043, filed Jan. 21, 2014, and claims priority of Japanese Patent Application No. 2013-021828 filed on Feb. 6, 2013.

TECHNICAL FIELD

The present invention relates to disposable pull-on diapers and in particular, to disposable pull-on diapers for younger babies.

BACKGROUND

Conventionally, pull-on diapers are known. For example, Patent Literature 1 discloses a disposable pull-on diaper including a bodily fluid absorbent panel lying in a crotch region, extending in a longitudinal direction and attached to sheet members forming respective interior surfaces of front and rear waist regions wherein the bodily fluid absorbent panel is disposed along both sides thereof with side flap portions and crotch elastics are attached under tension to free edge regions of these side flap portions. Lower elastics are attached under tension along leg-openings' peripheries defined by the front and rear waist regions, respectively.

CITATION LIST

Patent Literature

{PTL 1} JP 2009-61052 A

SUMMARY

Technical Problem

A pull-on diaper as disclosed in Patent Literature 1 is designed on the assumption that the diaper can be put on the infant's body in an upright posture or that the infant is in a growing phase capable of crawling on the hands and knees. Conventional designs of the diaper are based on the requirement that the waist of a wearer must be tightened to prevent the diaper from slipping down under the effect of gravity and/or mass of body waste. However, younger babies spend most of the day in a supine posture, neither stand up nor walk about, the legs are always spread in an M-shape and a joint is still underdeveloped. These characteristics are not observed in babies already in the growing phase capable of crawling on the hands and knees or standing up. For this reason, products for the younger babies have been limited to so-called tape-type diapers and none of pull-on diapers for the younger babies has been provided. The inventors have focused attention on the characteristics peculiar to the younger babies and devoted themselves to development of the pull-on diapers exclusively for younger babies based on findings from a study. Specifically, the inventors have arrived at a conclusion that, it is unnecessary for the diaper for the younger babies to tighten the waist to prevent the diaper from slipping down under the effect of gravity or mass of body waste; it is sufficient to put the absorbent structure in contact with the baby's body under a small pressure; and the respective leg-openings are preferably large so that the legs of the younger baby may not be stressed and so that mothers may not feel an anxiety when putting the diaper on the body of a younger baby. If the dimension of the respective leg-openings defined by the front and rear waist regions is enlarged in the conventional pull-on diaper as disclosed in PATENT LITERATURE 1, the elongation ratio of the lower elastics must be increased to achieve a desired fit about the thighs of the younger baby. However, increase of the elongation ratio of the lower elastics is inimical to the requirement for the diaper suitable for the younger baby as has been described above. It has been difficult to meet the requirement for ideal pull-on diapers exclusively for the younger baby and realization of the pull-on disposable diapers suitable for the younger baby is increasingly demanded.

An object of the present invention is to provide a disposable pull-on diaper, which is preferable to use for younger babies, being adapted to be easily put on without stressing the legs spread in an M-shape of a younger baby in a supine posture and without making a mother experience an anxiety. As used herein, the term "younger baby" refers to an early month old child, and more specifically, any child from one to twelve month old, especially one under eight month old, such as one before neither standing up nor crawling about on one's hands and knees. As used herein, the term "older baby" refers to an infant except the younger baby, i.e., a late month old child.

Solution to Problem

According to the present invention, there is provided a pull-on diaper having a transverse direction and a longitudinal direction being orthogonal to each other and including: a front waist panel; a rear waist panel both extending in the transverse direction: and a crotch panel extending in the longitudinal direction and joined to the front and rear waist panels, wherein: a plurality of waist elastics extending in the transverse direction are contractibly secured under tension to the front and rear waist panels, respectively; first leg elastics are contractibly secured under tension to lateral portions of the crotch panel, lateral portions of the front waist panel are joined to associated lateral portions of the rear waist panel in respective seam regions so that respective outer end portions of the front and rear waist panels form a waist-opening periphery; and respective inner end portions of the front and rear waist panels cooperate with the lateral portions of the crotch panel to define a pair of leg-openings' peripheries.

In the pull-on diaper for younger baby, a distance dimension between the upper end portions of the front and rear waist panels is in a range of 300 mm to 400 mm as measured on the diaper flatly developed after coupling of the front and rear waist panels in the seam regions has been released, and a distance dimension between a waist elastic closest to the inner end portion of the front waist panel among the waist elastics extending in the front waist panel across the respective seam regions in the front waist panel and a waist elastic closest to the inner end portion of the rear waist panel among the waist elastics extending in the rear waist panel across the respective seam regions is at least 55% of the distance dimension between the respective outer end portions of the front and rear waist panels.

Advantageous Effects of Invention

In the pull-on diaper for younger babies according to the present invention, the distance dimension between the outer end portions of the front and rear waist panels is in a range of 300 mm to 400 mm, and the distance dimension between the waist elastic among the waist elastics on the side of the front waist panel extending across the seam regions which lies closest to the inner end portion of the front waist panel and the waist elastic among the waist elastics on the side of the rear waist panel extending across the seam regions which lies closest to the inner end portion of the rear waist panel is at least 55% of the distance dimension between the outer end portions of the front and rear waist panels. With such dimensioning, the extensibility of the leg-openings through which the infant's legs are put is increased and, consequently, the pull-on diaper may readily allow the legs spread in an M-shape of a younger baby in a supine posture to put through the leg openings.

DESCRIPTION OF EMBODIMENTS

Figure 1:
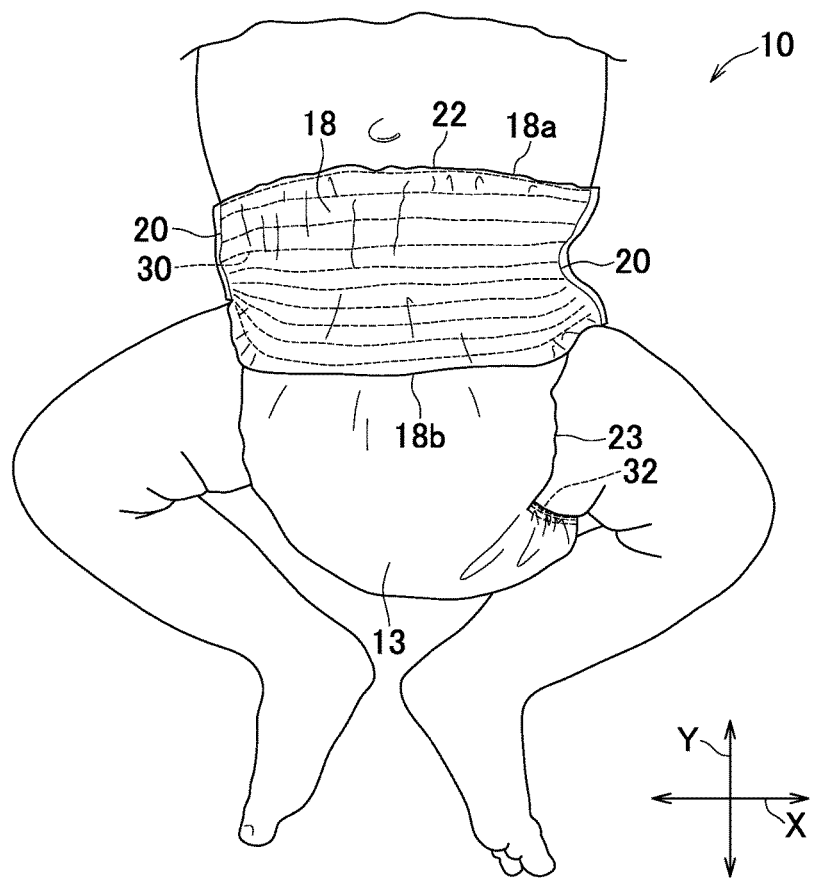
FIG. 1 is a perspective view exemplifying a pull-on diaper for younger babies.
Figure 2:
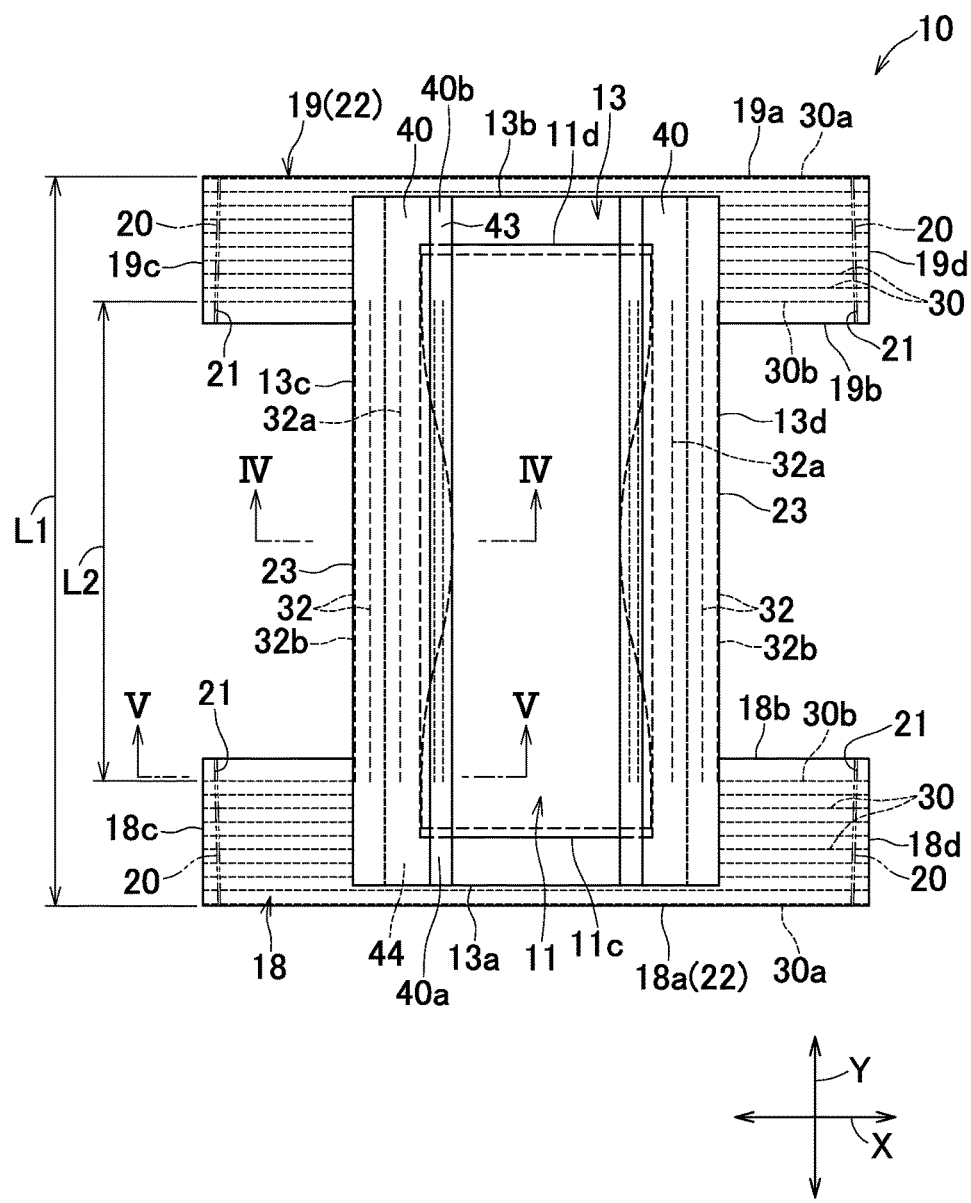
FIG. 2 is a partially cutaway plan view illustrating the pull-on diaper in flatly developed state.

Referring to FIGS. 1 and 2, a disposable diaper 10 has a transverse direction X and a longitudinal direction Y which are orthogonal to each other, a skin-facing surface lying on a side facing the wearer's skin and a non-skin-facing surface lying on the side opposite to the skin-facing surface, and includes a front waist panel 18 and a rear waist panel 19 both extending in the transverse direction X and a crotch panel 13 extending in the longitudinal direction Y and attached to the front and rear waist panels 18, 19. Respective lateral portions of the front waist panel 18 and the rear waist panel 19 are coupled along a pair of seam regions 20 to form an annular waist panel. The crotch panel 13 has front and rear end portions 13a, 13b (See FIG. 2) attached to respective midportions of the front waist panel 18 and the rear waist panel 19. The diaper 10 further includes a waist-opening periphery 22 defined by an outer end portion 18a of the front waist panel 18 and an outer end portion 19a of the rear waist panel 19 and a pair of leg-openings' peripheries 23 defined by lateral portions 13c, 13d of the crotch panel 13, an inner end portion 18b of the front waist panel 18 and an inner end portion 19b of the rear waist panel 19.

FIG. 2 is a partially cutaway plan view illustrating the diaper 10 in a flatly developed state after coupling of the front waist panel 18 and the rear waist panel 19 along the seam regions 20 of the diaper as illustrated in FIG. 1 has been released. As illustrated in FIG. 2, the front waist panel 18 and the rear waist panel 19 have rectangular shapes which are the same in shape as well as in size. The front waist panel 18 has the outer end portion 18a and the inner end portion 18b both extending in the transverse direction X and lateral portions 18c, 18d extending orthogonally to the outer and inner end portions 18a, 18b. The rear waist panel 19 has the outer end portion 19a, the inner end portion 19b and lateral portions 19c, 19d extending orthogonally to the outer and inner end portions 19a, 19b. The lateral portions 18c, 18d of the front waist panel 18 and the lateral portions 19c, 19d of the rear waist panel 19 associated with those of the front waist panel 18 may be overlapped and coupled with each other with the use of the hot welding technique such as hot embossing/debossing or ultrasonic welding to define the waist-opening periphery 22 of the diaper 10 by the outer end portions 18a, 19a of the front and rear waist panels 18, 19. The front and rear waist panels 18, 19 are disposed with waist elastics 30 extending in the transverse direction X and contractibly attached thereto under tension, and the lateral portions 13c, 13d of the crotch panel 13 are disposed with first leg elastics 32 extending in the longitudinal direction Y and contractibly attached thereto under tension.

Figure 3:
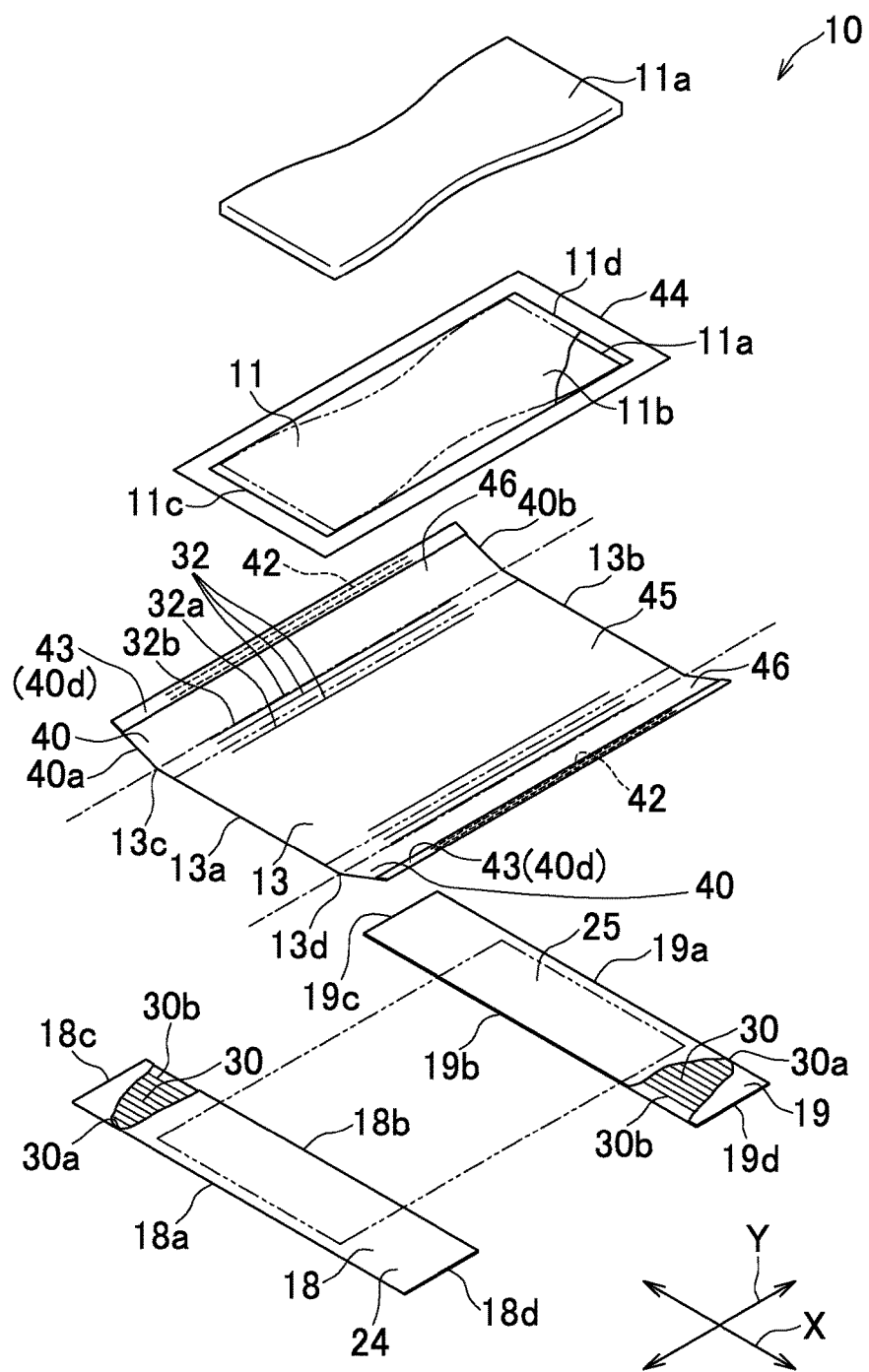
FIG. 3 is an exploded perspective view of the pull-on diaper.

Referring to FIG. 3, the front and rear waist panels 18, 19 are respectively formed of a front sheet 24 and a rear sheet 25 respectively doubled-up to interpose a plurality of waist elastics 30 extending in the transverse direction X between halve layers of the respective doubled-up sheets 24, 25 and to attach these waist elastics 30 to the respective waist panels 18, 19 under tension with the use of a hot melt adhesive. Alternatively, it is also possible to form the front and rear waist panels 18, 19 from an inner sheet lying on the skin-facing surface and an outer sheet lying on the non-skin-facing surface, respectively.

The front sheet 24 and the rear sheet 25 are formed preferably with the use of an air-permeable fibrous nonwoven fabric made of a thermoplastic resin or a plastic sheet. As the fibrous nonwoven fabric made of a thermoplastic resin or as the plastic sheet, one or more may be selected from, for example, an SMS (spunbond/meltblown/spunbond) fibrous nonwoven fabric, a spunbond nonwoven fabric, an air-through nonwoven fabric and an air-permeable plastic sheet each having a mass per unit area in a range of about 15 to about 30 g/m².

The waist elastics 30 extending in the transverse direction X in the front sheet 24 and the rear sheet 25 are formed of a plurality of strand- or string-like elastic materials and attached under tension between the opposed layers of the respective doubled-up front and rear sheets 24, 25. The waist elastics 30 attached to the front and rear waist panels 18, 19 in this manner extend in the front and rear waist panels 18, 19 in the transverse direction X across the seam regions after the front and rear waist panels 18, 19 are coupled with each other. Of these waist elastics 30 extending across the seam regions, the respective waist elastics 30a closest to the respective outer end portions 18a, 19a of the front and rear waist panels 18, 19 extend so as to overlap the respective outer end portions 18a, 19a. Of these waist elastics 30 extending across the seam regions 20, the respective waist elastics 30b closest to the respective inner end portions 18b, 19b extend in the transverse direction X at a distance of 5 to 10 mm from the respective inner end portions 18b, 19b. As a plurality of the elastic materials, for example, rubber strings having a fineness in a range of 310 to 620 dtex, preferably in a range of 400 to 600 dtex may be used. These rubber strings may be interposed between the respective opposed layers of the doubled up front and rear sheets 24, 25 and attached to the respective sheets 24, 25 under tension at an elongation ratio in a range of 2.0 to 3.5, preferably in a range of 2.0 to 2.5, more preferably in a range of 2.2 to 2.3. The waist elastics 30 function to fit the front and rear waist panels 18, 19 to the waist of the younger baby. Skin of the younger baby is more delicate than the skin of an older baby and, in consideration of this, the elongation ratio of the waist elastics 30 is preferably lower than the elongation ratio in the diaper for the older baby. As used herein, the term "younger baby" refers to an early month old child, and more specifically, any child from one to twelve month old, especially one under eight month old, such as one before neither standing up nor crawling about on one's hands and knees. As used herein, the term "older baby" refers to an infant except the younger baby, i.e., a late month old child.

Referring to FIGS. 2 and 3, the crotch panel 13 has a rectangular shape and includes a back sheet 44, an absorbent structure 11 attached to the skin-facing surface of the back sheet 44 and an outer cover 45 attached to the non-skin-facing surface of the back sheet 44. The crotch panel 13 has, in addition, front and rear end portions 13a, 13b extending in the transverse direction X and lateral portions 13c, 13d extending in the longitudinal direction Y wherein the respective non-skin-facing surfaces of the front and rear end portions 13a, 13b of the crotch panel 13 are attached to midportions of the respective skin-facing surfaces of the front waist panel 18 and the rear waist panel 19 with the use of a hot melt adhesive. According to this embodiment, the hot melt adhesive is distributed in a region defined between the front waist panel 18 and the rear waist panel 19 and between the front and rear end portions 13a, 13b of the crotch panel 13 in a pattern of stripes extending in parallel to the longitudinal direction Y (not shown). The lateral portions 13c, 13d of the crotch panel 13 are disposed with the first leg elastics 32 extending in the longitudinal direction Y attached thereto under tension. Furthermore, the crotch panel 13 is disposed on the skin-facing surface thereof with a pair of leg cuffs 40 extending in parallel to the lateral portions 13c, 13d.

The back sheet 44 has an area sufficient to cover the entire non-skin-facing surface of the absorbent structure 11 and is formed of a liquid-impermeable plastic film. The outer cover 45 partially constitutes both the inner surface and the outer surface of the diaper 10 and, in view of this, the outer cover 45 is preferably formed of an air-permeable and comfortable textured fibrous nonwoven fabric. The absorbent structure 11 includes an absorbent core 11a being a generally hourglass-shape which is concave inward in its midsection in the longitudinal direction Y and may be formed by wrapping well known bodily fluid absorbent materials such as fluff wood pulp and superabsorbent polymer particles (SAP) with tissue paper and covering the absorbent core 11a with a bodyside liner 11b made of a nonwoven fabric having liquid-permeability and flexibility. In this regard, the method of forming the absorbent structure 11 is not limited to such method. Front and rear end portions 11c, 11d of the absorbent structure 11 overlap with respective regions of the front and rear waist panels 18, 19 in which the waist elastics 30 exist and, in consequence, respective dimensions in the transverse direction X of the front and rear end portions 11c, 11d of the absorbent structure 11 may vary in response to elongation and contraction of the waist elastics 30.

A dimension in the transverse direction X of the outer cover 45 constituting the crotch panel 13 is larger than the corresponding dimension of the back sheet 44 and consequently the outer cover 45 includes a pair of extension portions 46 extending outward in the transverse direction X beyond the lateral edges of the back sheet 44 when the outer cover 45 is lapped on and attached to the back sheet 44. The absorbent structure 11 is defined between the pair of extension portions 46. In regions of the respective extension portions 46 extending along the lateral edges of the back sheet 44, a plurality of the first leg elastics 32 extending in the longitudinal direction Y are contractibly attached under tension to the outer cover 45 with the use of a hot melt adhesive. The first leg elastics 32 include an inside elastic 32a closest to the absorbent structure 11 as viewed in the transverse direction X and an outside elastic 32b most distant from the absorbent structure 11 as viewed in the transverse direction X.

Both lateral portions of the outer cover 45 are folded back with the skin-facing surface inside so as to form sleeves 43 within which a plurality of second leg elastics 42 are attached under tension to the outer cover 45 with the use of a hot melt adhesive. The sleeves 43 function as free edge portions 40d of the respective leg cuffs 40. For the first leg elastics 32 and the second leg elastics 42, the elastic materials similar to those for the waist elastics 30 may be used. An elongation ratio at which the first leg elastics 32 and the second leg elastics 42 are contractibly attached under tension may be in a range of 2.0 to 3.5. The elongation ratio at which the second leg elastics 42 are contractibly attached under tension is preferably set to a value 1.1 to 1.3 higher than the elongation ratio at which the waist elastics 30 are contractibly attached under tension. By increasing the elongation ratio, it is possible for the second leg elastics 42 to contract to a larger extent than the waist elastic 30, whereby the leg cuffs 40 fit the legs of the younger baby. In consequence, it is assured to prevent the bodily fluids from leaking out beyond the leg-openings' peripheries in spite of dimensioning the leg-openings relatively large so that the baby's legs may be smoothly put through the leg-openings.

Figure 4:
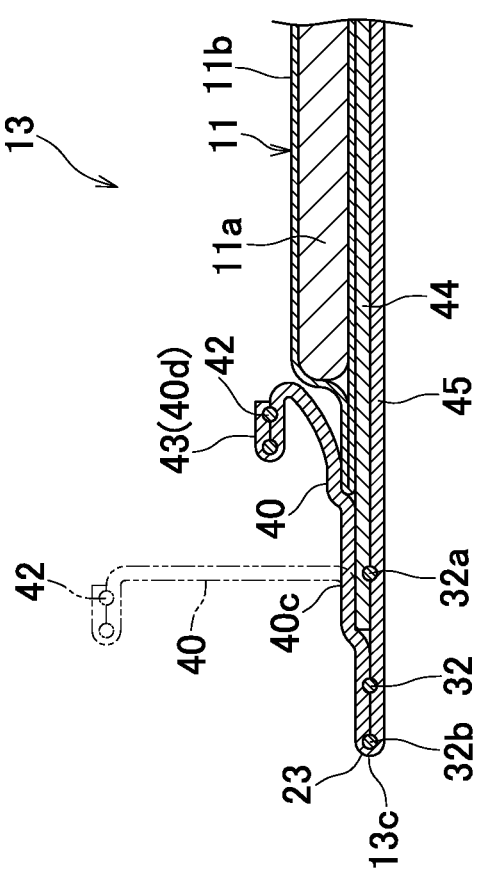
FIG. 4 is a schematic sectional view taken along line IV-IV in FIG. 2.
Figure 5:
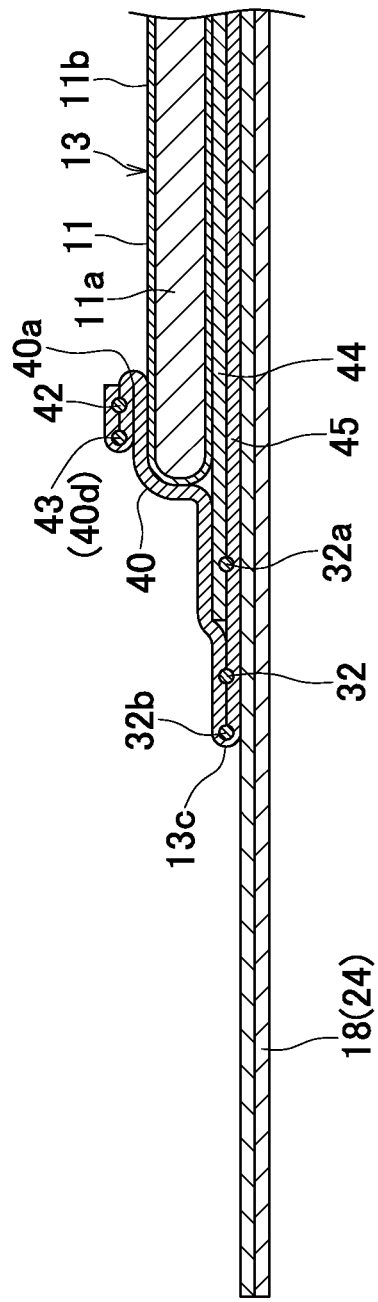
FIG. 5 is a schematic sectional view taken along line V-V in FIG. 2.

Referring to FIG. 4, the outer cover 45 is folded back along the outside elastic 32b with the skin-facing surface inside so that the first leg elastics 32 inclusive of the inside elastic 32a and the side edge of the back sheet 44 are interposed between layers facing each other of the folded back portion of the outer cover 45. Two layers of the outer cover 45 folded back and facing each other are attached to each other with the use of a hot melt adhesive in the range including the elastics from the outside elastic 32b to the inside elastic 32a. Referring to FIG. 3, folding lines of the outer cover 45 are indicated by dashed-dotted lines. With the diaper 10 put on the infant body, the regions in which the outer cover 45 has been folded back so as to interpose the outside elastic 32b under tension partially define the leg-opening peripheries 23 are kept in close contact with the thighs of the younger baby, thereby preventing leakage of bodily fluids. In this regard, a dimension in the transverse direction X of the crotch panel 13 corresponds to a distance between a pair of the outside elastics 32b as seen in a flatly developed planar view of the diaper 10.

The respective inside elastics 32a extending in the longitudinal direction Y substantially overlap with secured edge portions 40c of the associated leg cuffs 40 as seen in the planar view. The leg cuffs 40 extend along the lateral portions 13c, 13d of the crotch panel 13 and are adapted to be spaced apart from the bodyside liner 11b on respective proximal end portions defined by the secured edge portions 40c. Both end portions 40a, 40b of the leg cuffs 40 overlap with the front waist panel 18 and the rear waist panel 19, respectively, and the free edge portions 40d (sleeves 43) are folded back rearward of the diaper 10 and attached to the skin-facing surface of the absorbent structure 11 with the use of hot melt adhesive and thereby attached to the front waist panel 18 and the rear waist panel 19. Remaining portions of the respective leg cuffs 40 are not attached to any others and consequently rise from the crotch panel 13 as indicated by imaginary lines in FIG. 4 under contraction of the second leg elastics 42 when the diaper 10 is put on the baby's body. In addition, at the both end portions 40a, 40b, the free edge portions 40d are folded back rearward of the diaper and attached to the skin-facing surface of the absorbent structure 11. In consequence, the leg cuffs 40 easily collapse from upright states and make it possible to prevent the legs of the younger baby from being caught by the leg cuffs 40 when the diaper 10 is put on the body of the younger baby.

The elongation ratio of the second leg elastics 42 is preferably the same as that of the first leg elastics 32. In this way, the first leg elastics 32 and the second leg elastics 42 are kept in contact with the thighs of the younger baby under an equivalent contractile force, making it possible to improve a leak-preventing effect around the baby's thighs. From the other point of view, the contractile force necessary to assure desired fit to the thighs of the younger baby may be evenly distributed to the first leg elastics 32 and the second leg elastics 42 with the arrangement as described just above to avoid an anxiety that the skin of the infant might have gather traces due to the first leg elastics 32 or the second leg elastics 42. If the elongation ratio of the first leg elastics 32 is set to be higher than that of the second leg elastics 42, in the diaper 10 put on the younger baby, the second leg elastics 42 will sag and it will become difficult to keep the leg cuffs in close contact with the body of the younger baby. Consequently, not only the leakage preventing effect will be deteriorated but also urine and/or feces will be seen through the leg-openings as if leakage is occurring. In addition, the leg-openings' peripheries will be liable to be unacceptably tightened since the first leg elastics 32 primarily support the absorbent structure 11. In contrast, if the elongation ratio of the first leg elastics 32 is set to be lower than that of the second leg elastics 42, the first leg elastics 32 will not be kept in close contact with the body of the younger baby, leaving gaps between the first leg elastics 32 and the body of the younger baby and the leak preventing effect will be deteriorated. The second leg elastics 42 attached at the elongation ratio higher than that of the first leg elastics 32 will necessarily cause the leg cuffs 40 to dig into the crotch of the younger baby.

Referring again to FIG. 2, in the diaper 10 according to the present invention flatly developed after the coupling of the front waist panel 18 and the rear waist panel 19 along the seam regions 20 has been released, a distance dimension L1 between the respective outer end portions 18a, 19a of the front and rear waist panels 18, 19 is in a range of 300 mm to 400 mm. Of the waist elastics 30 extending across the respective seam regions 20, a distance dimension L2 between the waist elastic 30b lying closest to the inner end portion 18b of the front waist panel 18 and the waist elastic 30b lying closest to the inner end portion 19b of the rear waist panel 19 is at least 55% of the distance dimension L1 between the outer end portions 18a, 19a. Preferably, the distance dimension L2 is in a range of 60% to 80% of the distance dimension L1 and more preferably in a range of 60% to 70% of the distance dimension L1. The distance dimension L1 and the distance dimension L2 may be set to these ranges to improve an extensibility of the leg-openings' peripheries 23, thereby enlarging the leg-openings through which the baby's legs should be put when the diaper 10 is put on the body of the younger baby in a supine posture. In this way, it is possible to provide the pull-on diaper improved so that the legs spread in an M-shape of the younger baby can be smoothly put through the leg-openings. In this regard, if the distance dimension L2 is less than 55% of the distance dimension L1, it will be impossible to assure a sufficient extensibility of the leg-openings' peripheries 23, making it difficult to put the legs of the younger baby through the leg-openings. In contrast, if the distance dimension L2 exceeds 80% of the distance dimension L1, there will be possibility of leak beyond the leg-openings' peripheries 23. If the distance dimension L1 exceeds 400 mm, the crotch region will become bulky to deteriorate external appearance, the leg-openings' peripheries will be liable to leave a gap and the absorbent structure 11 will be unacceptably distanced from the urethral orifice, in consequence, leakage from the diaper may not be prevented effectively.

According to an embodiment of the present invention, a circumferential length of the respective leg-openings' peripheries is preferably in a range of 330 mm to 430 mm as measured when the first leg elastics 32 and the waist elastics 30 are in a stretched state. As used herein, the term "circumferential length of the leg-opening's periphery" means, for example, in the left side leg-opening's periphery 23 in FIG. 2, a length of the course extending from an intersection point of the waist elastic 30b closest to the inner end portion 18b of the front waist panel 18 and an inner side 21 of the seam region 20 via the waist elastic 30b closest to the inner end portion 19b of the rear waist panel 19 to an intersection point of the waist elastic 30b of the rear waist panel 19 and the inner side 21 of the seam region 20. As used herein, the term "the waist elastic 30b closest to the inner end portion 18b of the front waist panel 18" means the waist elastic 30b among the waist elastics 30 extending across the seam region 20 on the front waist panel 18 which lies closest to the inner end portion 18b of the front waist panel 18, and as used herein, the term "the waist elastic 30b closest to the inner end portion 19b of the rear waist panel 19" means the waist elastic 30b among the waist elastics 30 extending across the seam region 20 on the rear waist panel 19 which lies closest to the inner end portion 19b of the rear waist panel 19. This is true for the leg-opening periphery 23 on the right side of drawing sheet. If the circumferential length of the respective leg-openings' peripheries exceeds 430 mm, there will be high possibility that bodily fluids might leak beyond the leg-openings' peripheries and if the circumferential length is less than 330 mm, it will be difficult to put the legs through the leg-openings when the diaper 10 is put on the body of the younger baby.

According to another embodiment of the present invention, a circumferential length of the waist-opening's periphery 22 is preferably in a range of 550 mm to 650 mm as measured when the waist elastics 30 are in a stretched state. As used herein, the term "circumferential length of the waist-opening" means the circumferential length extending from the inner side 21 of the seam region 20 and, more specifically, the circumferential length extending from the inner side 21 of either seam region 20 via the outer end portions 18a, 19a of the front and rear waist panels 18, 19 back to the inner side 21 of the starting seam region 20. If the circumferential length of the waist-opening's periphery 22 exceeds 650 mm, it will be necessary to increase the elongation ratio of the waist elastics 30 for fit to a delicate body of the younger baby but this is undesirable since there is a possibility that compression traces might be marked on the waist of the younger baby. If the circumferential length of the waist-opening's periphery 22 is less than 550 mm, it will become difficult to put the legs spread in an M-shape through the leg-openings when the diaper 10 is put on the younger baby.

According to still another embodiment of the present invention, the dimension in the transverse direction X of the crotch panel 13 is at least 50% of the dimension of the front and rear waist panels 18, 19 and preferably in a range of 50% to 70%. If this dimension ratio is less than 50%, there is a high possibility that gaps might be created between the legs spread in an M-shape of the younger baby and the crotch panel 13 and cause leakage of bodily fluids. In this regard, as used herein, the term "dimension in the transverse direction X of the front and rear waist panels 18, 19" means the minimum distance between the inner sides 21 of a pair of the seam regions 20 in the front waist panel 18 or the rear waist panel 19 as measured on the flatly developed diaper 10. As used herein, the term "dimension in the transverse direction X of the crotch panel 13" means the length dimension between the lateral portions 13c, 13d of the crotch panel 13 as measured on the flatly developed diaper 10.

There is an anxiety that bodily fluids might leak beyond the peripheries of the leg-openings when the leg-openings of the diaper 10 are dimensioned to be relatively large so that the legs spread in an M-shape of the younger baby may be smoothly put through the leg-openings. However, such manner of dimensioning is preferable so long as leakage is effectively prevented by the leg cuffs. As has been described above, the elongation ratio of the second leg elastics may be set to be higher than that of the waist elastics and the leg cuffs may be designed to be easily collapsed outwardly of the diaper 10 to make the leakage preventing effect and the convenience to put the diaper 10 on the baby compatible with each other.

While the pull-on diaper 10 for the younger baby composed of the rectangular front and rear waist panels 18, 19 and the crotch panel 13 have been exemplified above, the present invention is not limited to this. For example, the inner end portions 18b, 19b of the front and rear waist panels 18, 19 may be shaped so as to protrude downward in a trapezoidal shape or an arc-shape. While the case in which the front waist panel 18 and the rear waist panel 19 have the same dimension in the longitudinal direction Y has been described, it is also possible, for example, to shape the front and rear waist panels 18, 19 so that the rear waist panel 19 is larger than the front waist panel 18.

The constituents of the diaper 10 are not limited to those described in the specification but the other various types of material widely used in the relevant technical field may be used without limitation unless otherwise stated. As used herein, the term "attached with the use of a hot melt adhesive" means that the hot melt adhesive may be distributed in various well known patterns such as spiral-, dotted- or stripe-pattern for bonding.

The disclosure of the present invention described hereinabove may be arranged at least in the following features:

A pull-on diaper having a transverse direction and a longitudinal direction being orthogonal to each other and including: a front waist panel; a rear waist panel both extending in the transverse direction; and a crotch panel extending in the longitudinal direction and coupled with the front and rear waist panels, wherein:

a plurality of waist elastics extending in the transverse direction are contractibly attached under tension to the front and rear waist panels, respectively;

first leg elastics are contractibly attached under tension to lateral portions of the crotch panel;

lateral portions of the front waist panel are coupled with associated lateral portions of the rear waist panel in respective seam regions so that respective outer end portions of the front and rear waist panel may form a waist-opening periphery; and respective inner end portions of the front and rear waist panels cooperate with the lateral portions of the crotch panel to define a pair of leg-openings' peripheries;

a distance dimension between the outer end portions of the front and rear waist panels is in a range of 300 mm to 400 mm as measured on the diaper flatly developed after coupling of the front and rear waist panels in the seam regions has been released; and a distance dimension between the waist elastic closest to the inner end portion of the front waist panel among the waist elastics extending in the front waist panel across the respective seam regions in the front waist panel and the waist elastic closest to the inner end portion of the rear waist panel among the waist elastics extending in the rear waist panel across the respective seam regions is at least 55% of the distance dimension between the respective outer end portions of the front and rear waist panels.

The present invention disclosed above may at least include the following embodiments, which may be taken in isolation from or in combination with one another:

(1) The pair of the leg-openings' peripheries respectively have a circumferential length in a range of 330 mm to 430 mm as measured when the first leg elastics and the waist elastics are in a state under tension.

(2) A circumferential length of the waist-opening's periphery is in a range of 550 mm to 650 mm as measured when the waist elastics are in a state under tension.

(3) A dimension ratio in the transverse direction of the crotch panel to the dimension in the transverse direction of the front and rear waist panels is at least 50%.

(4) An elongation ratio of the first leg elastics is higher than an elongation ratio of the waist elastics.

(5) As viewed in the diaper flatly developed after the coupling of the lateral portions of the front and rear waist panels has been released, the crotch panel is disposed along the lateral portions thereof with a pair of leg cuffs including secured edge portions, free edge portions and both end portions being orthogonal to the secured edge portions and the free edge portions, wherein second leg elastics are contractibly attached under tension to the free edge portions and, at the both end portions, the free edge portions are folded back outward in the transverse direction of the diaper and attached to the front and rear waist panels.

(6) The elongation ratio of the first leg elastics is equal to the elongation ratio of the second leg elastics.

The invention claimed is:

1. A pull-on diaper having a transverse direction and a longitudinal direction being orthogonal to each other, the pull-on diaper comprising: a front waist panel extending in the transverse direction; a rear waist panel extending in the transverse direction; and a crotch panel extending in the longitudinal direction and coupled with the front and rear waist panels, wherein a plurality of waist elastics extending in the transverse direction are contractibly attached under tension to the front and rear waist panels, respectively, first leg elastics are contractibly attached under tension to lateral portions of the crotch panel, lateral portions of the front waist panel are coupled with associated lateral portions of the rear waist panel in respective seam regions, the front and rear waist panels have outer end portions, respectively, said outer end portions defining a waist-opening periphery; inner end portions, respectively, said inner end portions cooperating with the lateral portions of the crotch panel to define a pair of leg-openings' peripheries, a first distance dimension between the outer end portions of the front and rear waist panels in the longitudinal direction is in a range of 300 mm to 400 mm as measured on the diaper flatly developed after coupling of the front and rear waist panels in the seam regions has been released, a second distance dimension between (i) the waist elastic closest to the inner end portion of the front waist panel among the waist elastics extending in the front waist panel across the respective seam regions in the front waist panel and (ii) the waist elastic closest to the inner end portion of the rear waist panel among the waist elastics extending in the rear waist panel across the respective seam regions in the longitudinal direction is at least 55% of the first distance dimension between the outer end portions of the front and rear waist panels, an elongation ratio of the first leg elastics is higher than an elongation ratio of the waist elastics, as viewed in the diaper flatly developed after the coupling of the lateral portions of the front and rear waist panels has been released, a pair of leg cuffs including secured edge portions and free edge portions is disposed along the lateral portions of the crotch panel, the pair of leg cuffs further includes secured and free edge end portions opposing each other in the longitudinal direction, the secured and free edge end portions being orthogonal to the secured edge portions and the free edge portions, second leg elastics are extensibly attached under tension to the free edge end portions, wherein the free edge end portions are folded over the second leg elastics, and the free edge end portions are folded back outward, and at the secured and free edge end portions of the pair of leg cuffs, the free edge portions are folded back outward in the transverse direction and attached to the front and rear waist panels, and the elongation ratio of the first leg elastics is the same as an elongation ratio of the second leg elastics.

2. The diaper according to claim 1, wherein the pair of the leg-openings' peripheries respectively have a circumferential length in a range of 330 mm to 430 mm as measured when the first leg elastics and the waist elastics are in a state under tension.

3. The diaper according to claim 1, wherein a circumferential length of the waist-opening's periphery is in a range of 550 mm to 650 mm as measured when the waist elastics are in a state under tension.

4. The diaper according to claim 1, wherein a ratio of a dimension of the crotch panel in the transverse direction to a dimension of one of the front and rear waist panels in the transverse direction is at least 50%, and the dimension of one of the front and rear waist panels in the transverse direction is measured on the diaper flatly developed after the coupling of the lateral portions of the front and rear waist panels has been released while the plurality of waist elastics are in a state under tension.

5. The diaper according to claim 1, further comprising:

an absorbent core positioned at the crotch panel, wherein the second leg elastics overlap the absorbent core as viewed in the diaper flatly developed after the coupling of the lateral portions of the front and rear waist panels has been released.

6. The diaper according to claim 5, wherein the first leg elastics are disposed on outer sides of the second leg elastics in the transverse direction and do not overlap the absorbent core as viewed in the diaper flatly developed after the coupling of the lateral portions of the front and rear waist panels has been released.

* * * * *